United States Patent [19]

Kobayashi

[11] Patent Number: 5,737,641
[45] Date of Patent: Apr. 7, 1998

[54] VIEWPOINT DETECTING DEVICE USING STORED INFORMATION WHEN DETECTING IS IMPROPER

[75] Inventor: Takashi Kobayashi, Mitaka, Japan

[73] Assignee: Canon Kabushiki Kaisha, Tokyo, Japan

[21] Appl. No.: 507,078

[22] Filed: Jul. 26, 1995

[30] Foreign Application Priority Data

Jul. 29, 1994 [JP] Japan .................... 6-178566

[51] Int. Cl.⁶ .................................. G03B 17/00
[52] U.S. Cl. .................................. 396/51
[58] Field of Search .................. 354/62, 410, 219; 396/51

[56] References Cited

U.S. PATENT DOCUMENTS

| | | | |
|---|---|---|---|
| 4,950,069 | 8/1990 | Hutchinson | 351/210 |
| 5,182,443 | 1/1993 | Suda et al. | 354/219 |
| 5,214,466 | 5/1993 | Nagano et al. | 354/219 |
| 5,245,371 | 9/1993 | Nagano et al. | 354/219 |
| 5,280,312 | 1/1994 | Yamada et al. | 351/211 |
| 5,335,035 | 8/1994 | Maeda | 354/219 |
| 5,386,258 | 1/1995 | Nagano | 354/219 |
| 5,402,199 | 3/1995 | Akashi | 354/410 |
| 5,541,400 | 7/1996 | Hagiwara et al. | 354/410 |
| 5,541,655 | 7/1996 | Kaneda | 348/333 |
| 5,543,887 | 8/1996 | Akashi | 354/410 |

FOREIGN PATENT DOCUMENTS

| | | | |
|---|---|---|---|
| 1241511 | 9/1989 | Japan . | |
| 2-32312 | 2/1990 | Japan . | |
| 5285113 | 11/1993 | Japan | A61B 3/14 |
| 6034874 | 2/1994 | Japan | G02B 7/28 |
| 6138373 | 5/1994 | Japan | G02B 7/28 |
| 7031589 | 2/1995 | Japan | A61B 3/113 |

Primary Examiner—Russell E. Adams
Attorney, Agent, or Firm—Fitzpatrick, Cella, Harper & Scinto

[57] ABSTRACT

A viewpoint detection device comprises a viewpoint detection circuit which detects a position of viewpoint of an operator, a memory for storing detection information from the viewpoint detection circuit in a case where the position of the viewpoint is properly detected, and a correction circuit which compensates an output of the viewpoint detection circuit by using detection information stored in the memory, when the detection of the position of viewpoint is not conducted properly by the viewpoint detection circuit.

32 Claims, 13 Drawing Sheets

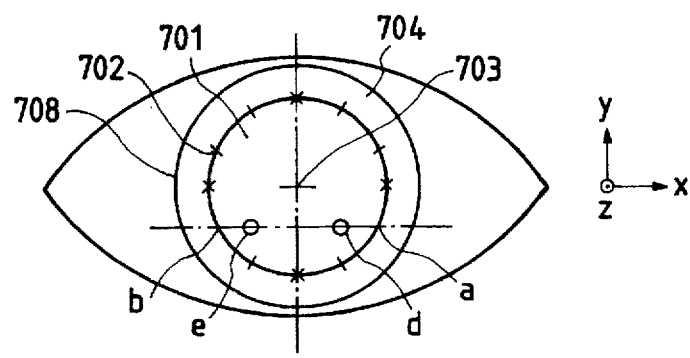
FIG. 1A
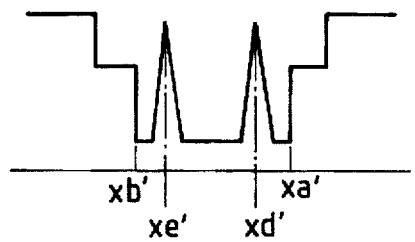
FIG. 1B
FIG. 1C
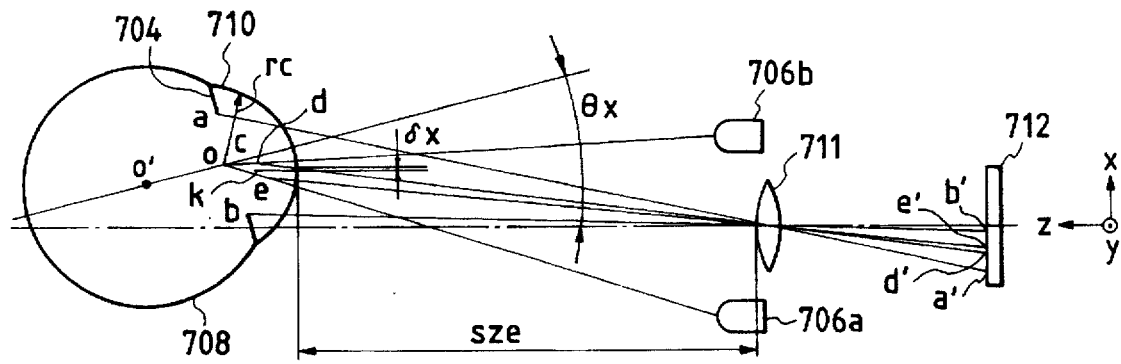
FIG. 1D
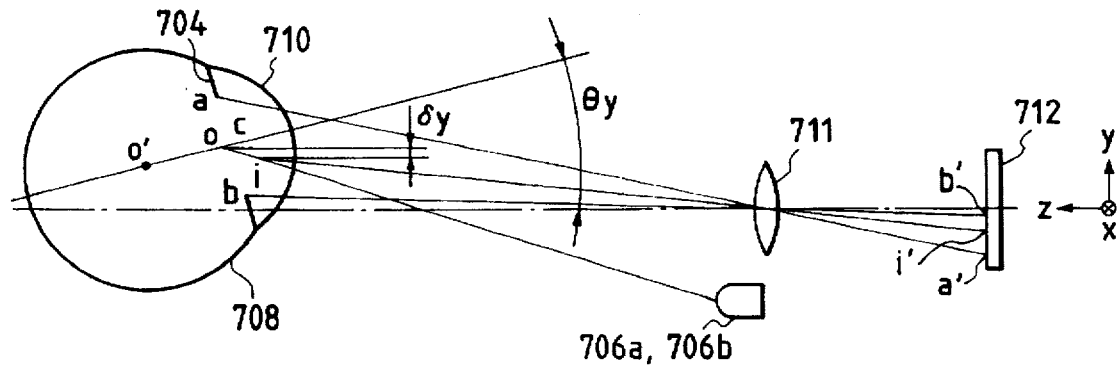

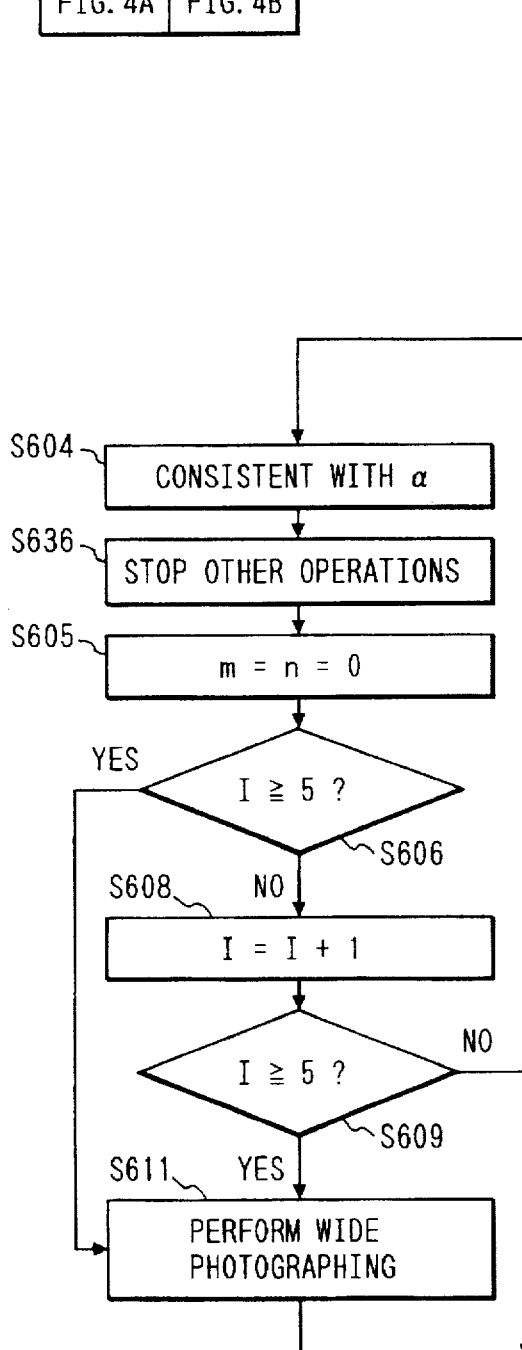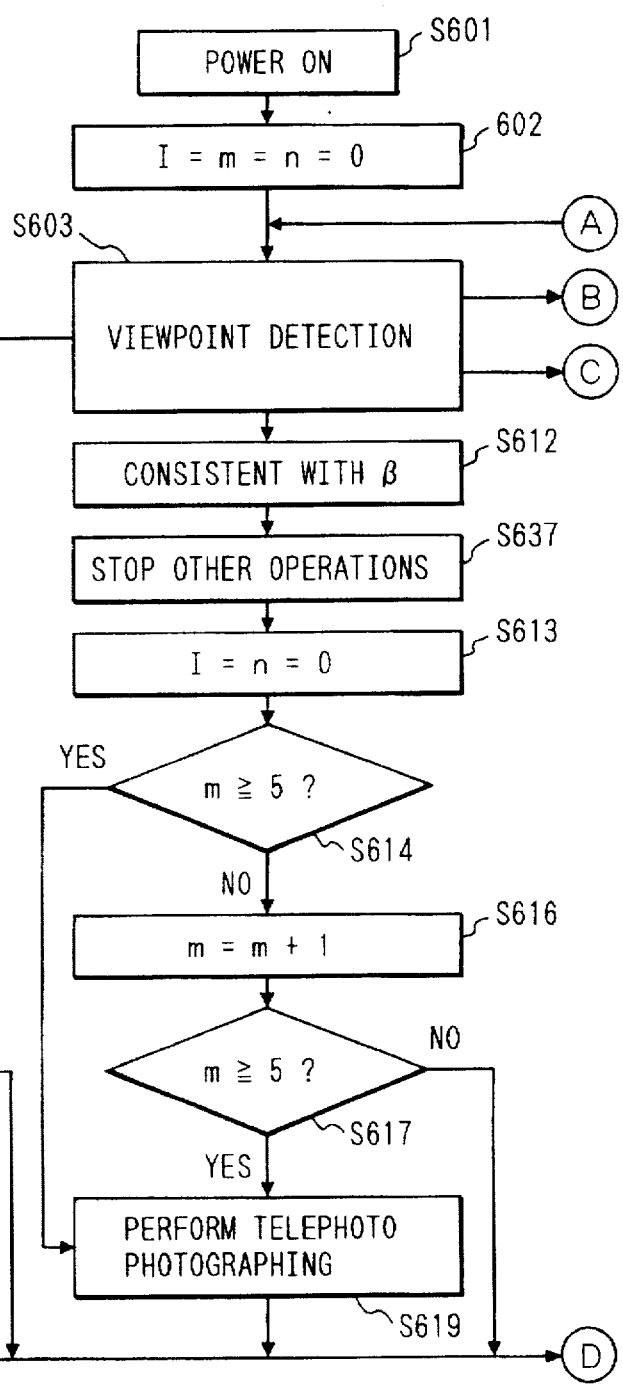

| FIG. 9A |
|---------|
| FIG. 9B |

VIEWPOINT DETECTING DEVICE USING STORED INFORMATION WHEN DETECTING IS IMPROPER

BACKGROUND OF THE INVENTION

1. Field of the Invention

The present invention relates to a viewpoint detecting device.

2. Related Background Art

Image equipment such as video camera have shown remarkable progress, in recent years, toward a smaller size and more diversified functions.

Along with such progress, for the purpose of reducing the cumbersome operations associated with such diversified functions and of achieving the operation intended by the operator, there is being introduced a viewpoint detecting device enabling the execution of various functions and the control of various operations by detecting the viewpoint of the operator.

Such a viewpoint detecting device, for example in the case of a camera such as a video camera, enables focusing to a position watched by the operator or activator of such functions as a switch for executing any of the camera functions when a corresponding index mark is watched by the operator.

In the following there will be explained an example of a video camera in which, as previously proposed by the assignee of the applicant, the viewpoint detecting device is utilized for lens focusing and zooming.

The video camera proposed by the assignee of the present applicant has a viewpoint input function detected by a viewpoint detecting device provided in the view finder, for achieving zooming operation by selecting zooming marks "TELE" and "WIDE" displayed on the finder image area, and a focusing further for focussing to an object at the viewpoint on said finder image area.

In the following there will be explained the principle of viewpoint detection in the viewpoint detecting device proposed by the assignee of the present applicant.

FIGS. 1C and 1D are respectively a plan view and a lateral view showing the principle of viewpoint detection.

Referring to FIGS. 1A to 1D, light sources 706a, 706b composed, for example, of infrared light emitting diodes (IRED) emitting infrared light, insensitive to the observer, are and positioned substantially symmetrical in the x (horizontal) direction with respect to the optical axis of an imaging lens 711 (cf. FIG. 1C) and somewhat lower in the y (vertical) direction (cf. FIG. 1D) and effect diverging illumination on the eye of the observer. A part of the illuminating light reflected by the eye 708 is focused by the imaging lens 711 onto an image sensor 712. FIG. 1A approximately shows the image of the eye projected on the image sensor 712, and FIG. 1B is a chart showing the output intensity of the image sensor 712.

Now, the principle of viewpoint detection will be explained with reference to these drawings.

At first, in the horizontal plane, the infrared light emitted from the light source 706b illuminates, as shown in FIG. 1C, the cornea 710 of the eye 708 of the observer. A corneal reflected image d (false image) formed by the infrared light reflected on the surface of the cornea 710 is condensed by the imaging lens 711 and is focused on a position d' on the image sensor 712. Similarly a corneal reflected image e (false image) formed by the infrared light reflected on the surface of the cornea 710 is condensed by the imaging lens 711 and is focused at a position e' on the image sensor 712.

Also, light beams from edges a, b of the pupil 701, surrounded by the iris 704 (FIG. 1A) are focused, through the imaging lens 711, at positions a', b' on the image sensor 712. In case the rotation angle θ of the optical axis of the eye 708 is small relative to the optical axis of the imaging lens 711, there can be determined, on the image sensor 712, a plurality of the x-coordinates xa, xb of the edges a, b of the pupil 701, as indicated by marks x in FIGS. 1A to 1D. Thus, the center xc of the pupil is calculated, utilizing the minimum square method on a circle.

On the other hand, the rotation angle θx of the eye 708 relative to the optical axis can be represented as follows, utilizing the x-coordinate xo of the center o of curvature of the cornea 710:

$$oc*\sin \theta x = xc - xo \tag{1}$$

Also xo can be determined in the following manner, in consideration of a predetermined correction value δx at the center k of the corneal reflected images d and e:

$$xk = (xd + xe)/2$$

$$xo = (xd + xe)/2 + \delta x \tag{2}$$

δx is a value geometrically determined from the method of installation of the device, distance to the eye etc., but the method of such determination will not be explained further. By substituting (1) in (2), θx can be determined as:

$$\theta x = arc \sin [[xc - \{(xd + xe)/2 + \delta x\}]/oc] \tag{3}$$

Also the coordinates of the feature points projected on the image sensor can be defined, with prime('), as follows:

$$\theta x = arc \sin [[xc' - \{(xd' + xe')/2 + \delta x'\}]/oc/\beta] \tag{4}$$

wherein β is a magnification determined by the eye distance sze to the imaging lens 711 and obtained in practice as a function of the distance |xd'−xe'| of the corneal reflected images.

In the vertical plane, there is obtained a configuration as shown in FIG. 1D. The corneal reflected images formed by the two IRED's 706a, 706b are in a same position yi. The rotation angle θy of the eye 708 can be calculated in a similar manner as in the horizontal plane, except for the equation (2) which is replaced by the following equation (5) defining the y-coordinate yo of the center o of curvature of the cornea:

$$yo = yi + \delta y \tag{5}$$

wherein δy is a value determined geometrically from the method of installation of the device, the distance to the eye etc., but the method of such determination will not be explained further. Thus, the rotation angle θy in the vertical direction can be represented as:

$$\theta y = arc \sin [\{yc' - (yi' + \delta y')\}/oc/\beta] \tag{6}$$

wherein yc' is the vertical coordinate of the pupil center on the image sensor.

Also the coordinate (xn, yn) of a position on the finder image area of the video camera can be defined, with a constant m determined by the view finder optical system, as follows in the horizontal and vertical planes:

$$xn = m*arc \sin [[xc' - \{(xd' + xe')/2 + \delta x\}]/oc/\beta] \tag{7}$$

$$y_n = m * \arcsin[\{yc' - (yi' + \delta y')\}/oc/\beta] \quad (8)$$

As will be apparent from FIGS. 1A and 1B, the detection of the pupil edges utilized an upshift (xb') and a down-shift (xa') of the output waveform of the image sensor. Also, the coordinates of the corneal reflected images are determined by sharp upshifts (xe', xd').

In the following there will be explained a viewpoint switch as an example of the viewpoint detecting device utilizing the above-explained principle.

FIG. 2 is a schematic block diagram of a video camera with viewpoint switch function.

The video camera shown in FIG. 2 is provided with a phototaking lens system 401 including a zoom lens for taking the image of an object; a view finder 403 containing a finder image area 402 for observing the object to be taken by the phototaking lens system 401; an eyepiece lens 404 provided in front of the view finder 403; viewpoint detecting means 406 for detecting the viewpoint of an eye 405 of the photographer; a display circuit 407 for displaying, on the image area 402, an AF frame approximately showing the focusing area, viewpoint switch marks to be explained later and other information such as tape counter and phototaking mode, required for the photographer; a system control circuit 408 for controlling various parts of the camera; a memory 409 for memorizing the coordinate values of the viewpoint switch marks on the finder image area; and an adder 410 for adding the outputs of the phototaking lens system 401 and the display circuit 407.

The above-mentioned viewpoint detecting means 6 is provided with an infrared light emitting diode 460 for irradiating the eye 405 of the photographer with infrared light; a dichroic mirror 461 transmitting the visible light but reflecting the infrared light; a condenser lens 462 for condensing the infrared light reflected by said dichroic mirror 461; a photoelectric converting element 463 for converting the infrared light, condensed by said condenser lens 462, into an electrical signal; and a viewpoint detecting circuit 464 for determining the viewpoint watched by the photographer on the finder image area, based on the image of the eye 405 of the photographer on said photoelectric converting element 463.

As the dichroic mirror 461 transmits the visible light, the photographer can observe the finder image area 402 through the eyepiece lens 404. Also as the dichroic mirror 461 reflects the infrared light, the reflected image of the eye 405, irradiated by the infrared light emitting diode 460, is condensed by the condenser lens 462 and focused on the photoelectric converting element 463.

The viewpoint detecting circuit 464 determines the viewpoint of the photographer on the finder image area 402, based on the image of the eye 405 on the photoelectric converting element 463, according to the above-mentioned principle or an algorithm disclosed in the Japanese Patent Laid-open Applications Nos. 01-241511 and 02-32312.

In the following there will be explained the functions of the viewpoint switch provided in the view finder 403 of the video camera equipped with the viewpoint detecting device.

An example of the display on the finder image area 402 is schematically shown in FIG. 3.

As shown in FIG. 3, there is display a menu consisting of index marks 501a, 501b, 501c represented by alphabets "W", "T" and "F" and indicating mutually different operations. For example "W" indicates the zooming operations toward the wide angle side, while "T" indicates that toward the telephoto side, and "F" indicates the fading operation. A numeral 502 at the lower right corner does not have the switching function but indicates, for example, a date.

In the following there will be explained an example of the function of the system control means 408, with reference to a flow chart shown in FIGS. 4A and 4B. Groups of coordinates of predetermined ranges including the visual switch index marks are memorized in a memory 409, and each group of coordinates includes all the coordinates within the range of each index mark shown in FIG. 3. These groups are represented for example by α, β and γ respectively for the zooming toward the wide angle side, the zooming toward the telephoto side and the fading. At first, when the power supply to the video camera is turned on (step S601), variables l, m and n are reset to zero (S602), whereby the viewpoint switches are made ready. The variables l, m, n respectively indicate the numbers of coincidences of the viewpoint of the photographer with any of the coordinates of the groups α, β and γ. While the photographer looks into the view finder and the viewpoint detection is executed properly (S603), the system control means 408 continuously receives the coordinates of the viewpoint of the photographer on the finder image area 402, from the viewpoint detecting circuit 464.

In the following there will be explained, as an example, the functions when the photographer watches the wide angle index mark "W". When the coordinates of the viewpoint approximately coincides with any of the coordinates in the group α (S604), the system control means 408 terminates any function other than the zooming operation toward the wide angle side (S636), then resets the variables m, n to 0 (S605) discriminates whether the variable l is at least equal to a predetermined number (5 in the present example) (S606), and, if less, adds 1 to l (S608). Then there is again discriminated whether l is at least equal to 5 (S609), and, if less, the sequence returns to the step S603 to receive the coordinates of the viewpoint from the viewpoint detecting circuit 464.

On the other hand, if the step S609 identifies that l is at least to 5, the zoom lens is shifted toward the wide angle side, and the sequence returns to the step S603 to receive the coordinates of the viewpoint again. If the step S606 identifies that l is at least equal to 5, the sequence jumps to a step S611. Even when the coordinates of the group α, if the coordinates of the viewpoint move outside the group α before the number of coincidences reaches 5, the variable l is reset to zero (S613, S621, S628). A similar procedure is executed also when the index mark "T" or "F" is looked at.

In the above-explained configuration, however, if the pupil is covered by the eyelid because of the inclination of the face of the photographer or of the eye movement, there cannot be obtained a plurality of the coordinates of the edges a, b of the pupil 601 shown in FIGS. 1A and 1B, so that the coordinates (xc, yc) of the pupil center can no longer be calculated, or contains a significant error even if it can be calculated, as will be explained further in the following.

FIG. 5 shows, as an example, a situation where the upper eyelid 804 partly covers the pupil so that the coordinates can only be obtained from the lower part of the pupil edge 801. 802 and 803 are corneal reflected images of the light sources, as explained in the foregoing principle. Now let us consider a case of determining the pupil edge from the eye image in such state, for example where the pupil edges can be detected in only two points in the lower part of the eye as shown in FIG. 6. As the pupil edge is detected in only two points, there can be considered many circles such as 902 and 903 that pass these two points and it is not possible to determine the pupil which is represented by a broken-lined circuit 901.

Also, even if more than two points can be defined on the pupil edge (as indicated by marks x in FIG. 7), but if a fluctuation exists in these points as shown in FIG. 7, the calculated pupil may become larger, as indicated by 1002, or smaller than the actual pupil 1001 because the upper edge is not available. Thus, the viewpoint detection based on the information of thus calculated pupil may result in a significant error.

SUMMARY OF THE INVENTION

In consideration of the foregoing, a first object of the present invention is to provide a viewpoint detecting method and a device therefore, capable of correcting the above-explained pupil information thereby reducing the error in the viewpoint detection.

A second object of the present invention is to provide a viewpoint detecting device capable of suppressing formation of correction error and reducing the error in the viewpoint detection.

A third object of the present invention is to provide an image pickup device capable of suppressing formation of the correction error and reducing the error in the viewpoint detection, even under a situation where the diameter of the pupil of the photographer varies frequently.

A fourth object of the present invention is to provide a viewpoint detecting device capable of reducing the measurement error in the calibration for personal fluctuation in the deviation between the inclination angle of the eye and the visual axis, specific to each person.

The above-mentioned objects can be attained, according to a preferred embodiment of the present invention, by a viewpoint detecting method of irradiating the eye of the user with light from a light source, detecting the position of the viewpoint of the eye from the reflected image thereof, and calculating the viewpoint of the line of sight of the user, wherein, in case the calculation of said viewpoint is conducted properly, the information representing the positional relationship of the corneal reflected image and the pupil or the iris is stored in memory means, and, in case said calculation of the viewpoint is not conducted properly, said information employed in the preceding calculation is read as correcting information from said memory means and the calculation of the viewpoint is conducted anew with said correcting information.

Also according to a preferred embodiment, there is provided a viewpoint detecting device in which the eye of the user is irradiated by light from a light source, the relative positional relationship between the corneal reflected image and the pupil or the iris is detected and the viewpoint of the line of sight of the user is calculated based on said positional relationship, comprising memory means for storing information representing said positional relationship in case said viewpoint calculation is conducted properly, and calculation means for reading, in case said viewpoint calculation is not conducted properly, said information employed in the preceding calculation as correcting information from said memory means and effecting the viewpoint calculation anew with said correcting information.

Also according to a preferred embodiment, there is provided a viewpoint detecting device wherein said memory means is adapted to always store latest information, and said calculation means is adapted to utilize said latest information as said correcting information.

Also according to a preferred embodiment of the present invention, there is provided an image pickup device provided with a viewpoint detecting device in which the eye of the user is irradiated by light from a light source, the relative positional relationship between the corneal reflected image and the pupil or the iris is detected and the viewpoint of the line of sight of the user is calculated based on said positional relationship, comprising memory means for storing said positional relationship employed in case said viewpoint calculation is conducted properly and luminance information of the taken image in this state, light amount detecting means for detecting the luminance of said taken image, and calculation means for reading, in case said viewpoint calculation is not conducted properly, the luminance information obtained from said light amount detecting means and the corresponding information representing said positional relationship as correcting information from said memory means and effecting viewpoint calculation anew utilizing said correcting information.

Also according to a preferred embodiment of the present invention, the above-mentioned viewpoint calculation is executed at the measurement of personal difference information for calibrating the personal fluctuation for example the deviation between the inclination angle of the eye and the visual axis, specific to each person.

Still other objects of the present invention, and the features thereof, will become fully apparent from the following description which is to be taken in conjunction with the attached drawings.

BRIEF DESCRIPTION OF THE DRAWINGS

FIGS. 1A to 1D are views showing the principle of viewpoint detection;

DETAILED DESCRIPTION OF THE PREFERRED EMBODIMENTS

Figure 2:
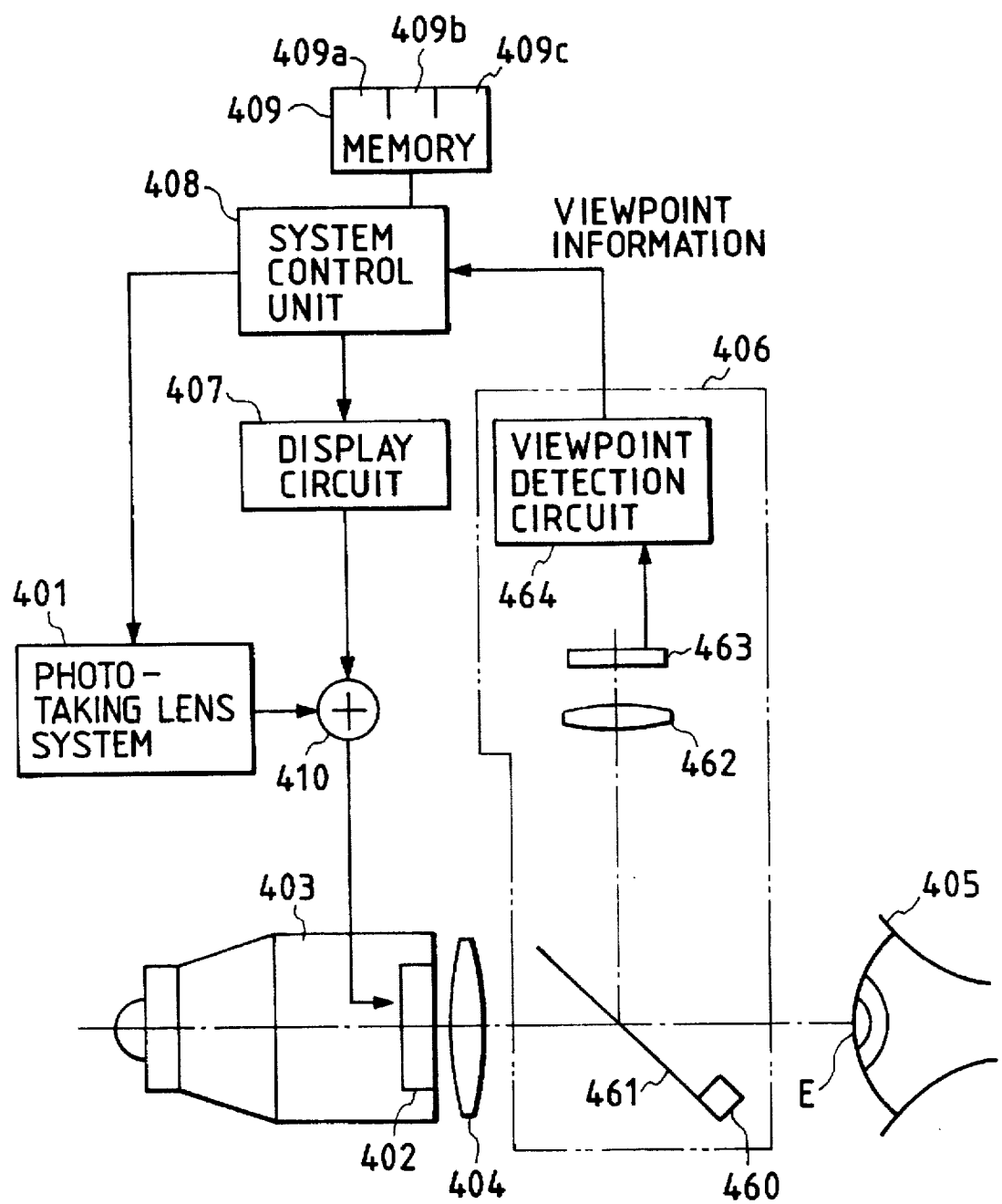
FIG. 2 is a block diagram of a viewpoint detecting device.
Figure 3:
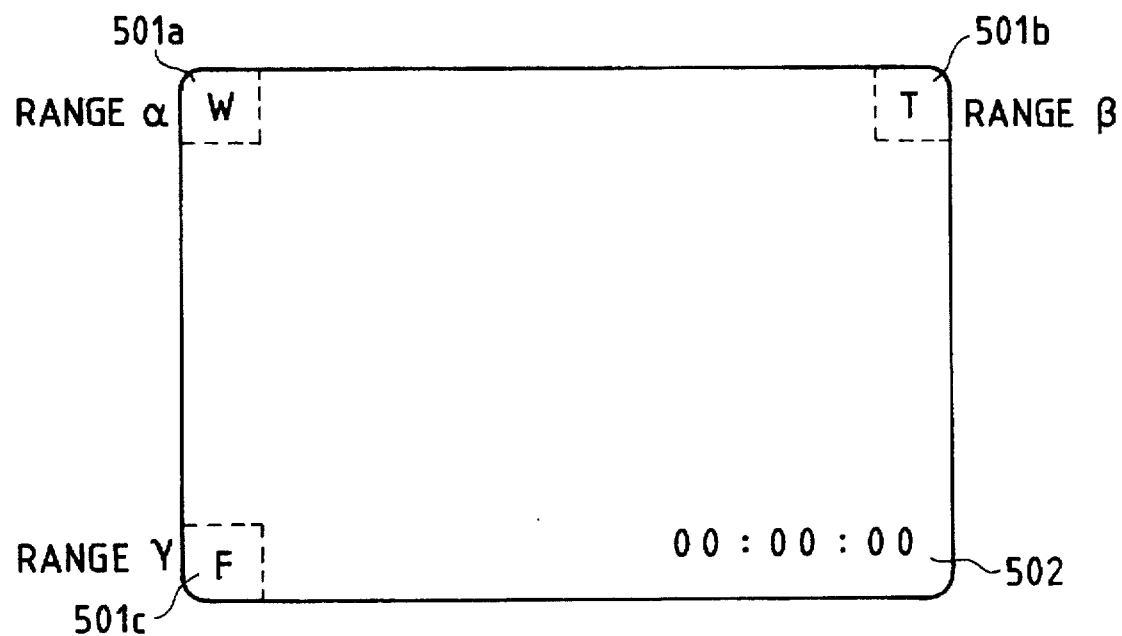
FIG. 3 is a schematic view of viewpoint switches utilizing the viewpoint detecting shown in FIG. 2.
Figure 5:
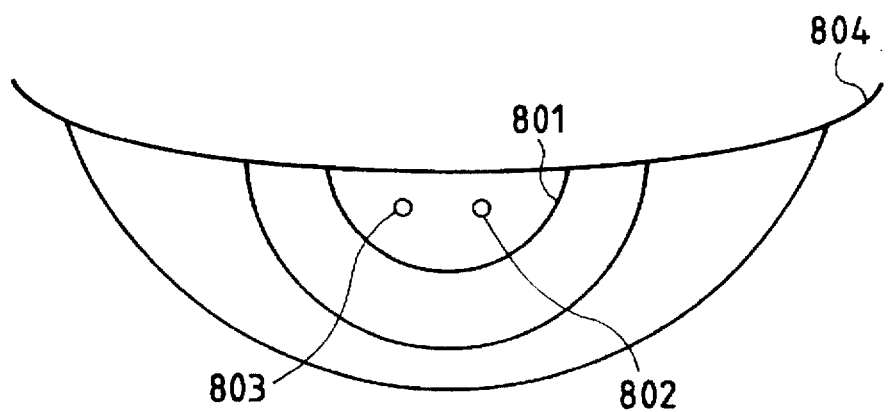
FIGS. 5 to 7 are views showing the drawback of the device shown in FIG. 3.
Figure 4B:
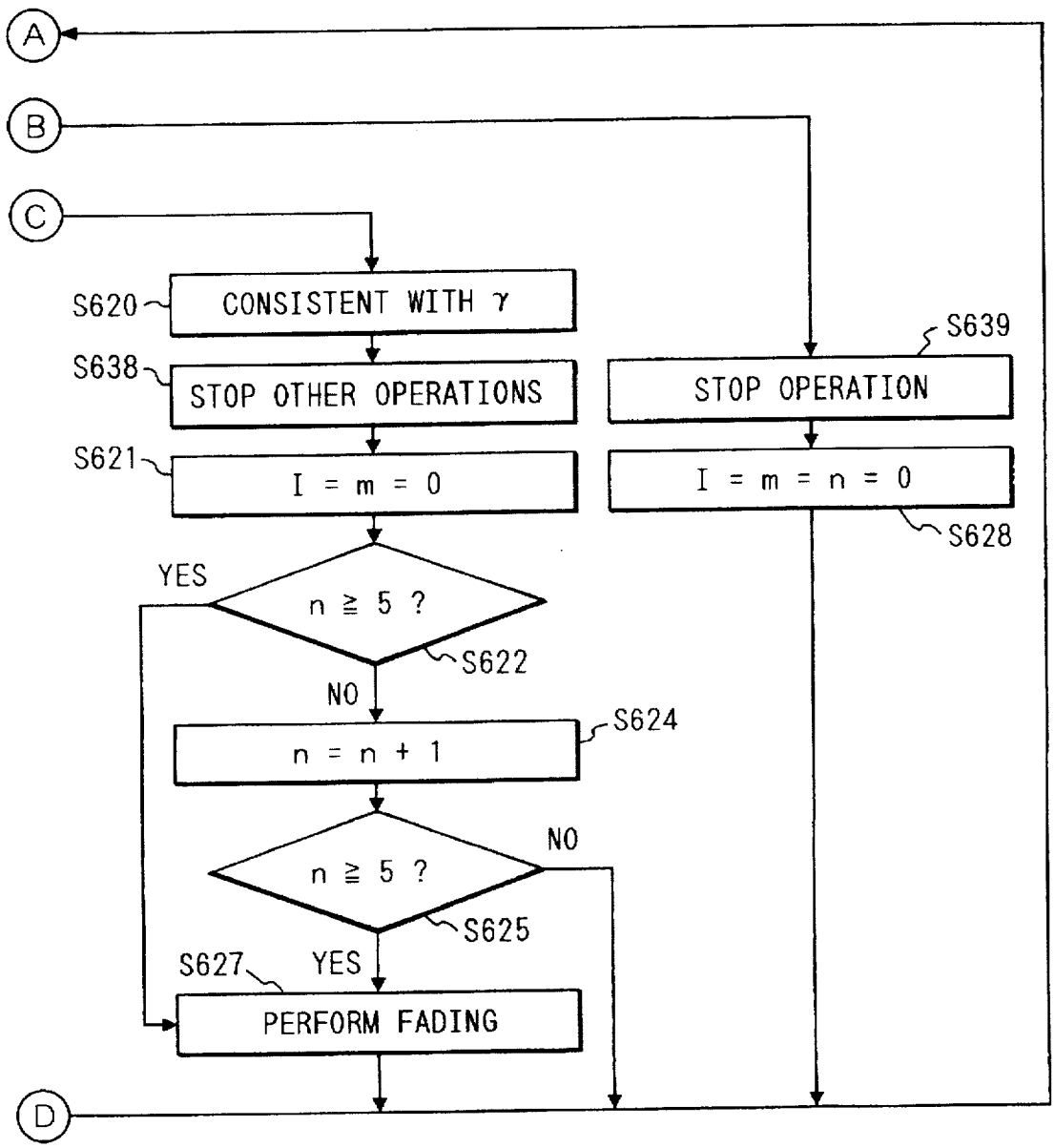
FIG. 4 which comprised of FIGS. 4A and 4B is a flow chart showing the control sequence of a viewpoint switch.
Figure 6:
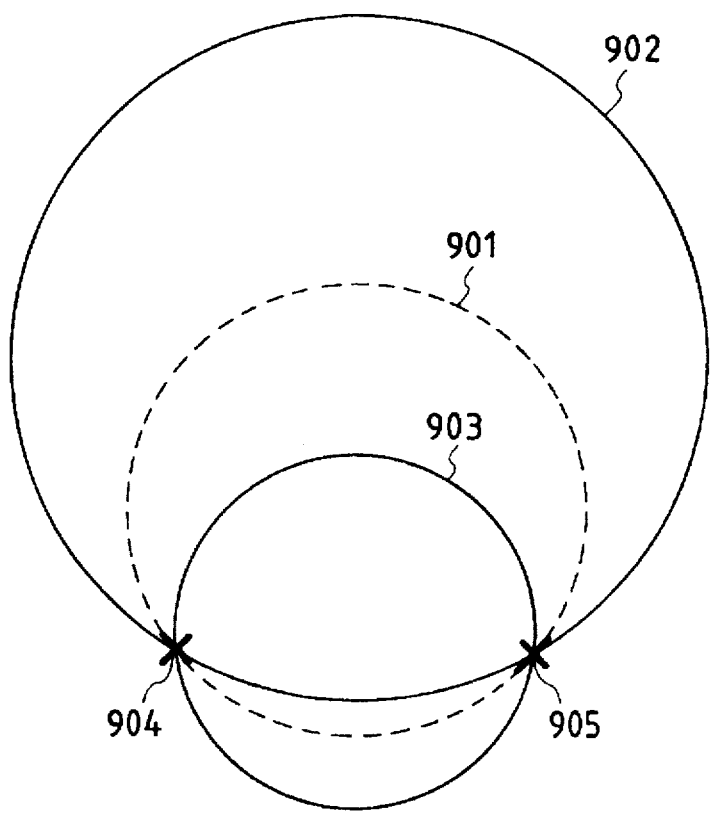
Figure 7:
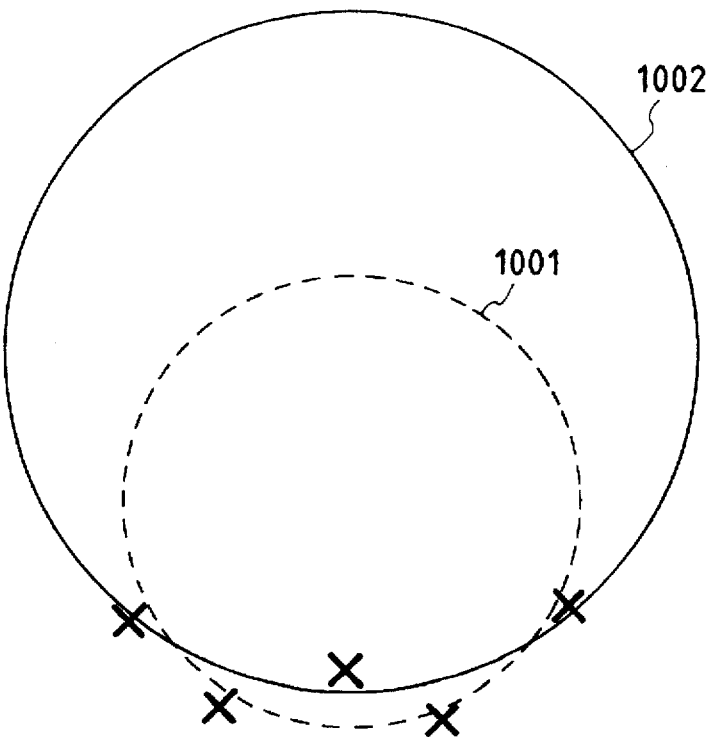
Figure 8:
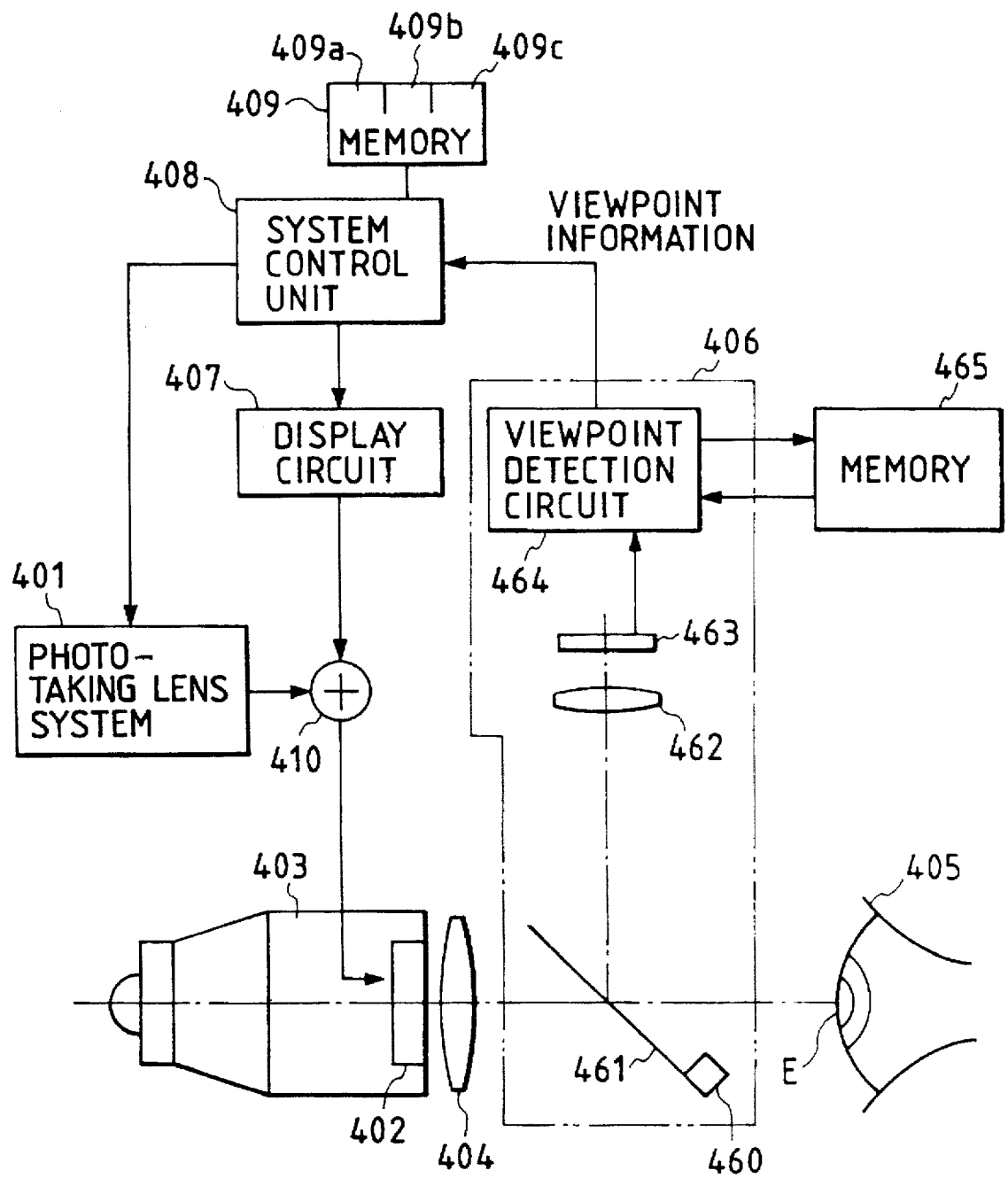
FIG. 8 is a block diagram of a viewpoint detecting device constituting a first embodiment of the present invention.

FIG. 8 is a block diagram of a video camera constituting a first embodiment of the present invention, wherein components equivalent in function to those in FIG. 2 are represented by the same symbols and will not be explained further. The circuit shown in FIG. 8 additionally contains a memory 465. In the following there will be explained the process executed by the viewpoint detecting circuit 464.

At first, when the user activates the viewpoint input function, a viewpoint detecting operation is repeated for every predetermined time interval T. After the user starts the viewpoint input function, the memory 465 stores a predetermined number of pupil diameters calculated from the pupil edge coordinates when the viewpoint detection was first possible. In case plural pupil edges cannot be obtained or the calculated viewpoint is identified as erroneous for example because of the aforementioned drawback, the viewpoint detection is conducted again utilizing the pupil diameter, stored in said memory 465, as correcting information.

Figures 9, 9A:
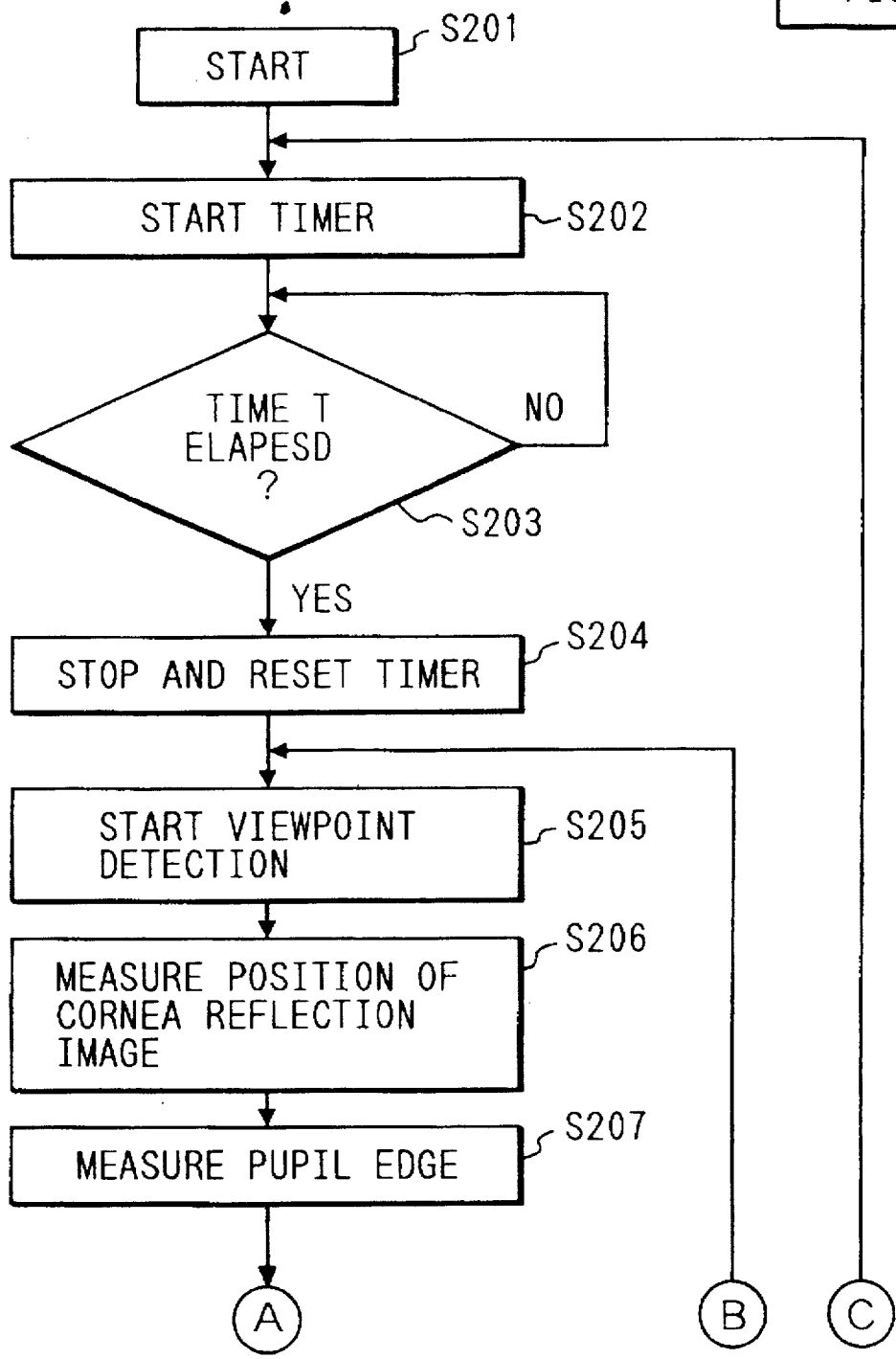
FIG. 9 which is comprised of FIGS. 9A and 9B is a flow chart showing the control sequence of a viewpoint detecting device of the first embodiment of the present invention.
Figure 9B:
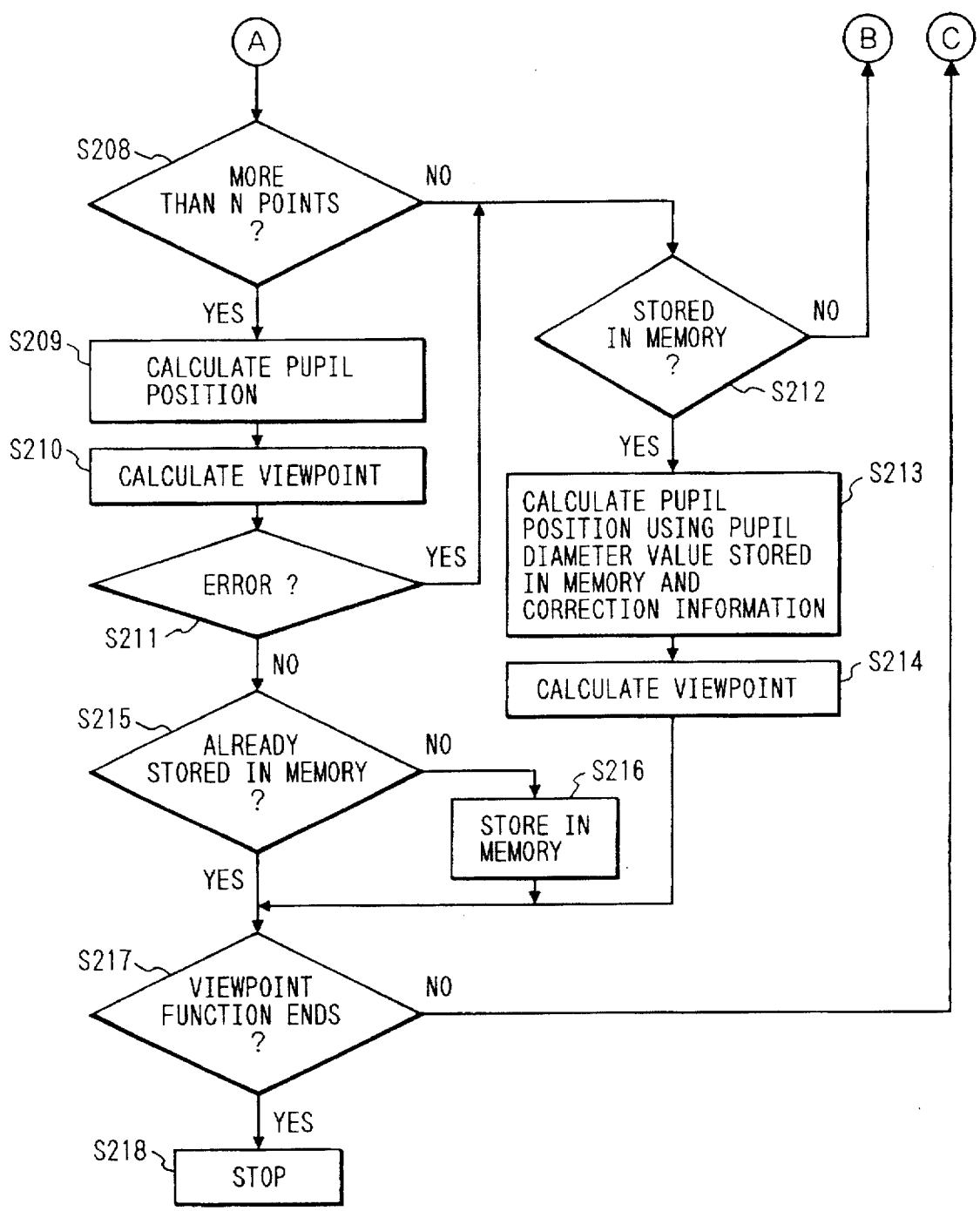

FIGS. 9A and 9B show flowcharts of the above-mentioned operation. When the user activates the viewpoint detecting device (S201), a timer is started (S202). After the lapse of a predetermined time T (S203), the timer is stopped and reset (S204), and the viewpoint detection is started (S205). At first there are conducted detection of the position of the corneal reflected image (S206) and detection of the pupil edge (S207), then there is discriminated whether the pupil edges have been obtained in at least predetermined n points (S208), and, if obtained, there are calculated the pupil position (S209) and the viewpoint (S210).

If the calculated viewpoint is identified as an error (S211), there is executed the process of a step S212. If the viewpoint is not identified as an error, the sequence proceeds to a step S215, and, if data are not stored in the memory 465, storage is conducted (S216). If the step S208 identifies that the pupil edges are less than the predetermined n points or if the step S211 identifies an error, the sequence proceeds to the step S212, and, if the memory 465 does not store the information on the pupil diameter, the sequence returns to the step S205 to repeat the detecting operation. If the memory 465 stores the information of the pupil diameter, it is used as the correcting information, for calculating the pupil position (S213) and the viewpoint is calculated (S214). If the function of the viewpoint detecting device is continued (S217), the sequence returns to S202.

In S211, the error in the viewpoint detection can be identified, for example, in case the pupil diameter calculated in the step S209 for determining the pupil position is significantly larger or smaller than the standard pupil diameter of human being, or in case the coordinate of the viewpoint calculated in the step S210 is positioned outside the viewfinder 402, or in case the distance between the finder 402 and the eye, calculated from the measurement of the corneal reflected image in the step S206 is longer than a predetermined value.

In the following there will be explained an example of the step S213 for calculating the pupil position, utilizing the correcting information in the memory 465.

Figure 10:
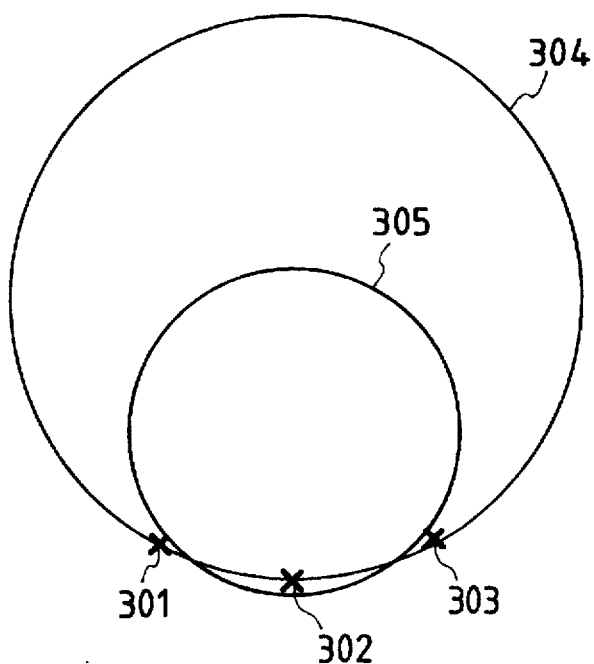
FIG. 10 is a schematic view showing the viewpoint calculation process in the first embodiment of the present invention.

Let us consider a situation where, as already explained in the drawback of the prior art, the upper portion of the pupil is covered by the upper eyelid, so that the pupil edge is obtained only in the lower part. Referring to FIG. 10, the edge is detected at three points 301, 302, 303 by the edge detection. It is assumed that the pupil 304, represented by a circle estimated by the minimum square method from these edge points, is larger than a predetermined pupil diameter. In such a case, the pupil can be determined, with a diameter stored in the memory 465, at a position minimizing the sum of the squares of the distances from the points 301, 302, 303.

In an example of such calculation, the error for the measured pupil edge (xi, yi) is represented by:

$$e=(xi-a)^2+(yi-b)^2-c^2 \qquad (9)$$

wherein (xi, yi) are the coordinates of the measured pupil edge (i=1, 2, 3), (a, b) is the center of the pupil to be calculated, and c is the radius of the pupil, obtained by division with 2 of the pupil diameter stored in the memory 465. The sum E of the squared errors for all the detected edges is represented by:

$$E=\Sigma e^2=\Sigma[(xi-a)^2+(yi-b)^2-c^2]^2 \qquad (10)$$

and the central portion (a, b) of the pupil is obtained by solving simultaneous equations obtained by partially differentiating the equation (10) with variables a, b.

As explained in the foregoing, in case the center of the pupil cannot be calculated or the calculated viewpoint involves a significant error even if the center of the pupil can be calculated, because the pupil is partly covered with the eyelid due to the face inclination or the eye movement of the user so that the pupil edges a, b cannot be obtained in plural points, the viewpoint is calculated utilizing, as the correcting information, the information required in recognizing the preceding pupil position in which the detection error was not identified as significant, and the detection error can be reduced in this manner.

Figures 11, 11A:
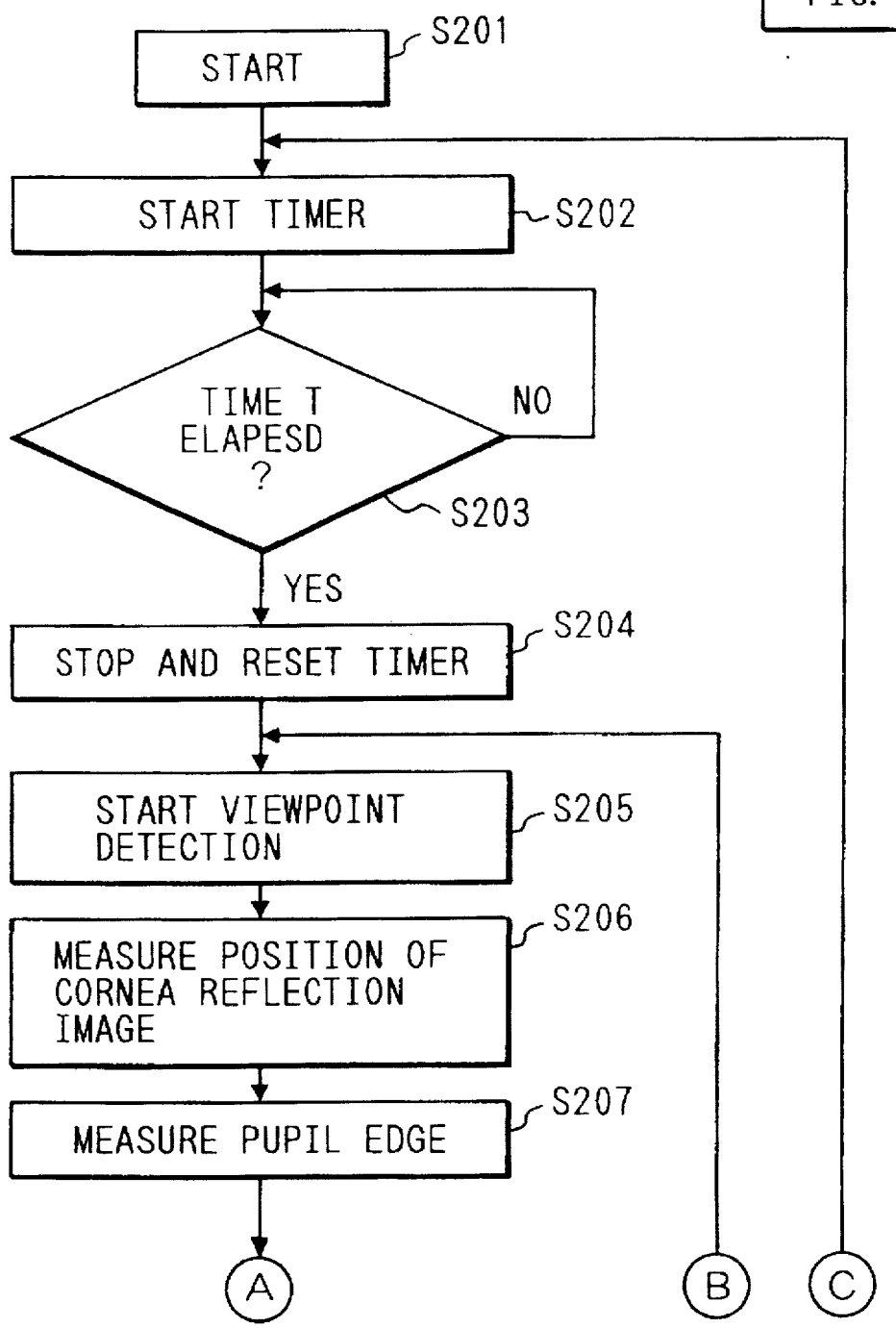
FIG. 11 which is comprised of FIGS. 11A and 11b is a flow chart showing the control sequence of a viewpoint detecting device constituting a second embodiment of the present invention.
Figure 11B:
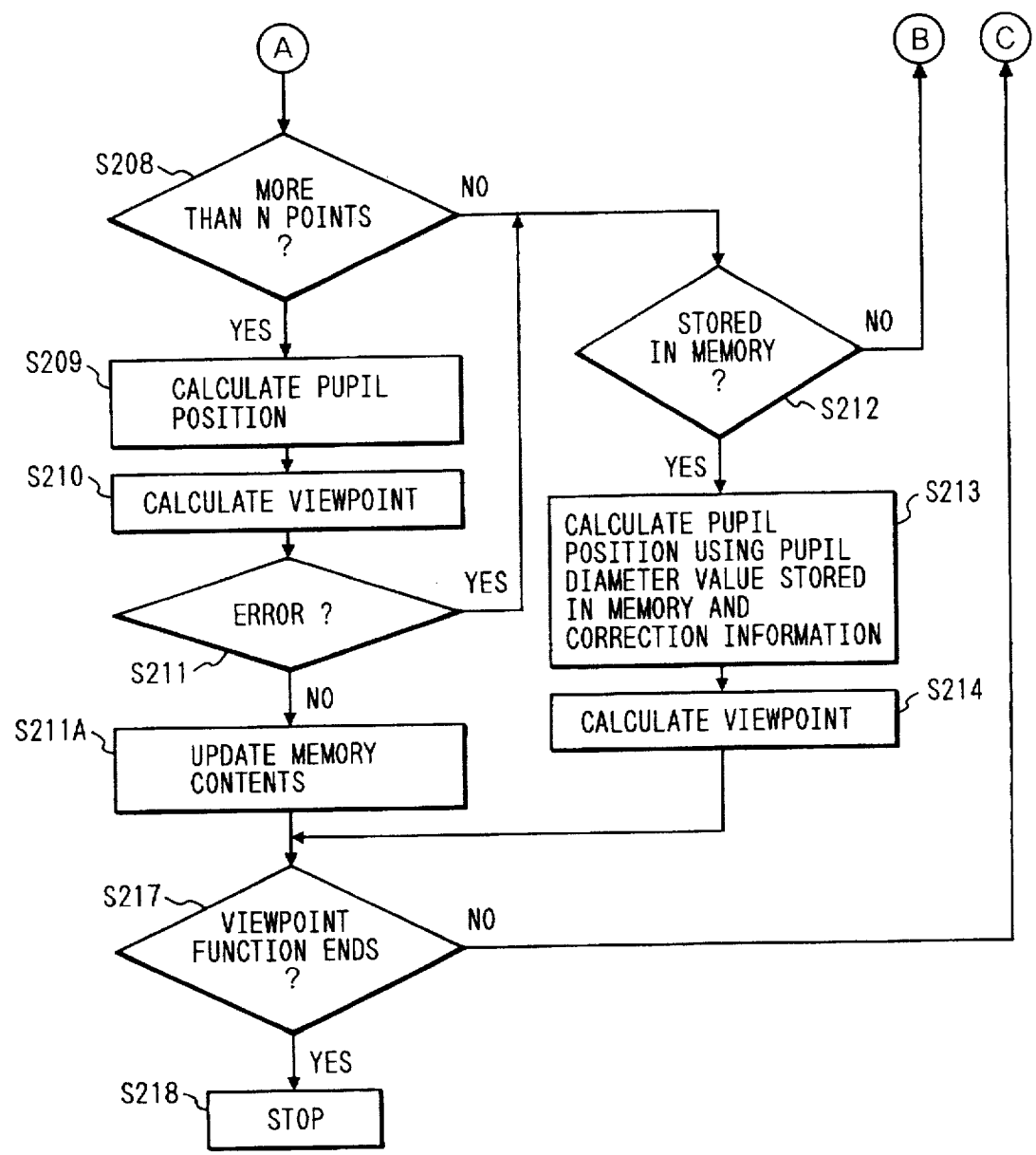

In the first embodiment explained above, if the repeating interval T of detection is sufficiently short (for example the interval of the vertical synchronization signal of the video signal), the image taken by the video camera and displayed on the view finder is anticipated to have a high correlation between the fields, so that the pupil diameter of the user is also anticipated to have a high correlation in viewpoints different in time. Consequently, in a second embodiment, the information of the pupil diameter stored in the memory 465 in the first embodiment is selected as the latest information before the viewpoint detection error is identified. FIGS. 11A and 11B show the control sequence in said second embodiment.

In FIGS. 11A and 11B, the steps S201 to S214, S217 and S218 are the same as those in the first embodiment shown in FIGS. 9A and 9B. In the flow shown in FIG. 11B, the steps S215 and S216 in FIG. 9B are omitted and a step S211A is newly added.

The step S211A always renews the information of the memory 465 whenever no error is identified in the viewpoint detection, regardless whether the pupil diameter is stored in the memory 465. Other functions are the same as those in the first embodiment. Thus, the correcting information consists of the latest information of the pupil diameter, before the viewpoint detection error is identified.

Thus, the second embodiment can reduce the detection error of the viewpoint while suppressing generation of a correction error, by employing, as the correcting information, a pupil diameter, which has a high correlation with the pupil diameter when the viewpoint detection error is identified.

In phototaking with the video camera of the first embodiment, some objects may frequently vary their light amount. Also, light and dark objects fields are often taken in a mixed manner, for example, by a panning or tilting operation. In such a situation, the luminance of the image in the view finder varies according to the luminance of the object to be taken, so that the pupil diameter of the user also varies frequently. In such a case, as the correcting information, there is employed a pupil diameter employed in the viewpoint detection of an image of which the luminance is as close as possible to that of the image when the viewpoint detection error is identified.

Figure 12:
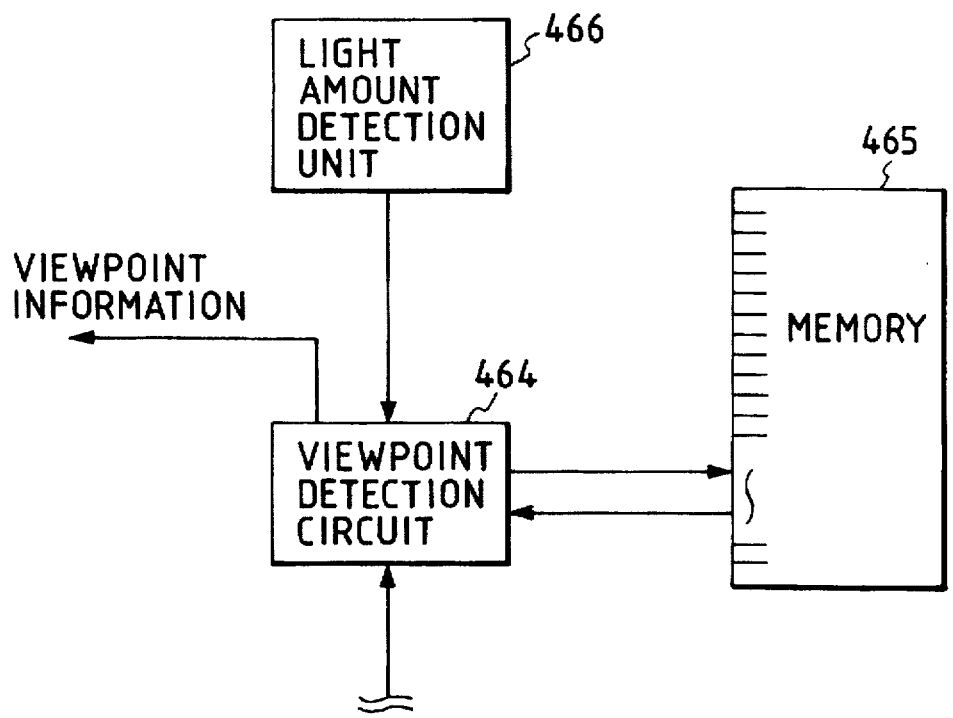
FIG. 12 is a block diagram of a part of a viewpoint detecting device constituting a third embodiment of the present invention.

FIG. 12 is a block diagram of a third embodiment of the present invention, wherein components corresponding to those in FIG. 8 are represented by the same symbols. Newly added light amount detecting means 466 can be AE (auto exposure) means provided in the phototaking lens system 401 of the video camera, or may be composed separately of a phototransistor or an image sensor for measuring the amount of light entering the video camera. The memory 465 stores the light amounts of the images and the pupil diameters in the past k cycles where the viewpoint detection was possible.

Figure 13:
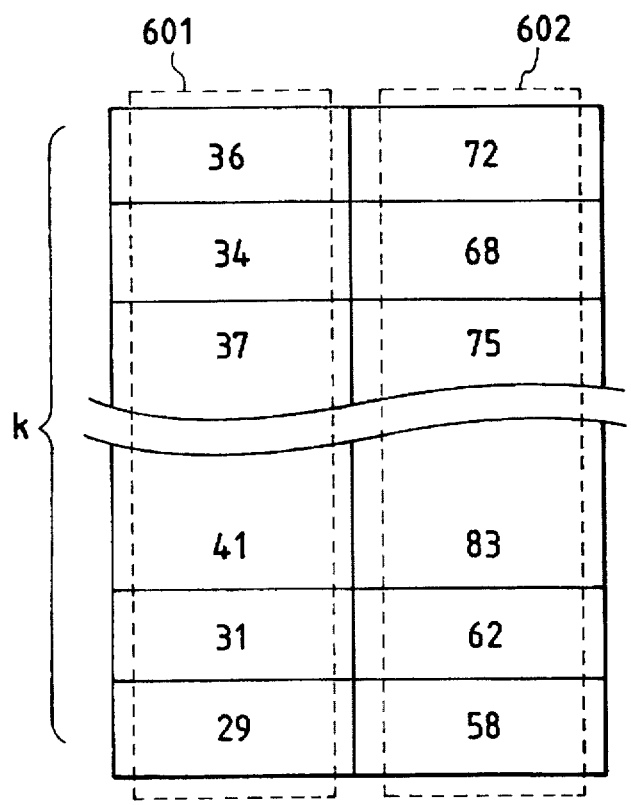
FIG. 13 is a schematic view of a memory in the viewpoint detecting device of the third embodiment of the present invention.

The number k can be selected arbitrarily. If a viewpoint detection error, due to a detection error in the pupil position, is identified, the viewpoint detecting circuit 464 obtains the luminance of the currently taken image from the light amount detection means 466 and reads, from the memory 465, the pupil diameter of an image of which the luminance is closest to the above-mentioned luminance. An example of the content of the memory 465 is shown in FIG. 13.

An area 601 stores averaged IRE values of different frames as the image luminances, while an area 602 stores the pupil diameters (in the unit of 0.1 mm) corresponding to the respective image luminances. If the luminance of the image taken when the above-mentioned error is identified, is for example 37 IRE, a pupil diameter of 75 (×0.1 mm) is employed as the correcting information. Other components in FIG. 12 function same as in FIGS. 1A to 1D.

The above-explained third embodiment reduces the error in the viewpoint detection and the error in correction, even under a situation where the pupil diameter of the user varies frequently.

A fourth embodiment effects, in the viewpoint detection explained above, calibration for correcting the personal fluctuation, such as the deviation between the inclination angle of the eye and the visual axis, specific to each user.

Figure 14:
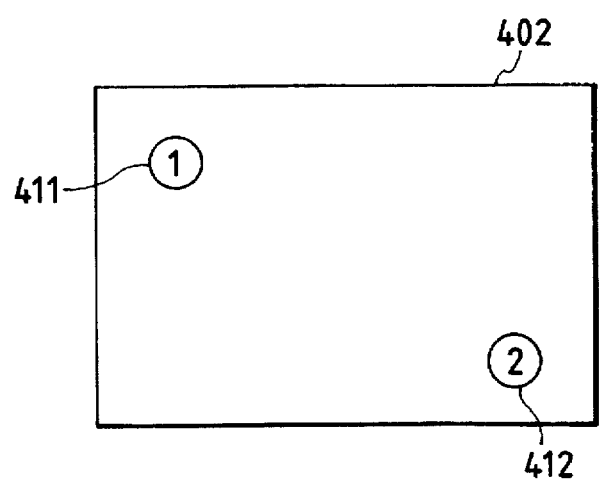
FIG. 14 is a schematic view showing the principle of measurement of personal difference information.

FIG. 14 shows an example of the display on the finder image area 402 for effecting the calibration, wherein two index marks 411, 412 are displayed in two points on the finder image area 402. The user watches the marks 411, 412 in succession for effecting the viewpoint detection, and the information on the personal fluctuation is obtained from the deviations between the coordinates of the index marks on the image area 402 and the measured coordinates of the viewpoints.

For example, in watching the lower mark 412 on the image area 402, the eye is directed downwards so that a part of the pupil may be covered by the eyelid and the pupil position may not be identified. In such case the pupil diameter employed in the viewpoint detection in watching the mark 411 is utilized as the correcting information, whereby the measurement in the calibration can be reduced. The method of correction is similar to that in the foregoing embodiments.

Thus, the fourth embodiment can reduce the measurement error in the calibration for correcting the personal fluctuation such as the deviation between the eye inclination angle and the visual axis, specific to each user.

The above-explained embodiments reduce the error in the viewpoint detection, by storing the information utilized in the calculation of the viewpoint, and, in case the calculation, is identified as improper because the information required for recognition of the position of the pupil or the iris is not measurable or the calculated viewpoint is significantly erroneous, calculating the viewpoint utilizing, as the correcting information, the stored information required for recognition of the position of the pupil or the iris.

Also, the above-explained embodiments reduce the error in the viewpoint detection while suppressing formation of the correction error, by storing the latest information as the above-mentioned correcting information, and, in case the calculation is identified as improper because the information required for recognition of the position of the pupil or the iris is not measurable or the calculated viewpoint is significantly erroneous, calculating the viewpoint with said latest correcting information.

Also, the above-explained embodiments reduce the error in the viewpoint detection while suppressing formation of the correction error, even under a situation where the pupil diameter of the user varies frequently, by storing the information employed in the viewpoint calculation and the luminance information of the taken image, and, in case calculation is identified improper because the information required for recognition of the position of the pupil or the iris is not measurable or the calculated viewpoint is significantly erroneous, calculating the viewpoint utilizing the correcting information corresponding to an image of which the luminance is closest to that of the image taken by the image pickup device.

Also, the above-explained embodiments effect viewpoint calculation at the calibration of the personal fluctuation such as the deviation between the eye inclination angle and the visual axis, specific to each user, thereby effecting plural viewpoint calculations, and, in case the calculation is identified as improper because the information required for recognition of the position of the pupil or the iris is not measurable or the calculated viewpoint is significantly erroneous, calculating the viewpoint utilizing said stored information as the correcting information, thereby reducing the measurement error in such a calibration.

What is claimed is:

1. A viewpoint detecting device comprising:
   a) viewpoint detecting means for taking an image of the eye of the user and detecting the position of the viewpoint of said user;
   b) memory means for storing information used for a first detecting operation of the viewpoint by said viewpoint detecting means when said viewpoint is properly detected by said viewpoint detecting means; and
   c) correction means for, when the viewpoint of the user is not properly detected by said viewpoint detecting means, causing said viewpoint detecting means to detect the viewpoint of the user by reading the information stored in said memory means.

2. A viewpoint detecting device according to claim 1, further comprising illumination means for illuminating the eye of said user, wherein said viewpoint detecting means is adapted to detect said viewpoint by receiving the light emitted by said illumination means and reflected by the surface of said eye.

3. A viewpoint detecting device according to claim 1, wherein said viewpoint detecting means is adapted to detect said viewpoint based on a corneal reflected image and the light reflected from the pupil or the iris.

4. A viewpoint detecting device according to claim 3, wherein the information stored in said memory means comprises information on the pupil diameter.

5. A viewpoint detecting device according to claim 1, wherein said correction means includes error discrimination means for identifying an error in the viewpoint detection operation performed by said viewpoint detecting means, and wherein said error discrimination means is adapted to identify the error in the viewpoint detection operation in the case where the pupil diameter is an abnormal value.

6. A viewpoint detecting device according to claim 1, wherein said correction means includes error discrimination mean for identifying an error in the viewpoint detection operation performed by said viewpoint detecting means, and wherein said error discrimination means is adapted to identify the error in the viewpoint detection operation in the case where the coordinates of the detected viewpoint are positioned outside an image area.

7. A viewpoint detecting device according to claim 1, wherein said correction means includes error discrimination means for identifying an error in the viewpoint detection operation performed by said viewpoint detecting means, and wherein said error discrimination means is adapted to identify the error in the viewpoint detection operation in the case where the distance between the eye and an image area is abnormal.

8. A video camera provided with a viewpoint detecting function, comprising:
   a) monitor means for monitoring a photo taken image;
   b) viewpoint detecting means for detecting the position of the viewpoint of the user on an image area of said monitor means;
   c) memory means for storing the information used for a first detection operation of the viewpoint by said viewpoint detecting means when said viewpoint is properly detected by said viewpoint detecting means; and
   d) correction means adapted, in case the detecting operation of said viewpoint detecting means is not properly conducted, to cause said viewpoint detecting means to detect the viewpoint of the user by reading the information stored in said memory means.

9. A video camera according to claim 8, wherein said monitor means comprises an electronic view finder comprising illumination means for illuminating the eye of said user, and wherein said viewpoint detecting means is adapted to detect said viewpoint by receiving the light emitted by said illumination means and reflected by the surface of said eye.

10. A video camera according to claim 8, wherein said viewpoint detecting means is adapted to detect said viewpoint based on a corneal reflected image and the light reflected from the pupil or the iris.

11. A video camera according to claim 8, wherein the information stored in said memory means comprises information on plural pupil diameters.

12. A video camera according to claim 8, wherein said correction means includes error discrimination means for identifying an error in the viewpoint detection operation performed by said viewpoint detecting means, and wherein said error discrimination means is adapted to identify the error in the viewpoint detection operation in a case where the pupil diameter is an abnormal value, or in a case where the coordinates of the viewpoint are positioned outside an image area of said monitor means, or in a case where the distance between the eye and the image area is abnormal.

13. A video camera according to claim 8, wherein said correction means includes error discrimination means for identifying an error in the viewpoint detection operation performed by said viewpoint detecting means, and wherein said error discrimination means is adapted to correct the output of said viewpoint detecting means with the information stored in said memory means in a case where edges of the pupil are not detected in a predetermined number.

14. A video camera according to claim 13, wherein said memory means is adapted to renew the information stored therein in a case where the viewpoint is properly detected by said viewpoint detecting means.

15. A viewpoint detecting method for use in a viewpoint detecting device in which the eye of the user is irradiated by light from a light source, the relative positional relationship between the corneal reflected image of said eye and the pupil or the iris thereof is detected, and the viewpoint of the line of sight of said user is calculated utilizing said positional relationship, comprising steps of:
   storing information representing said positional relationship in a memory means in case where said calculation of the viewpoint is properly conducted; and
   reading, in a case where said calculation of the viewpoint is not conducted properly, the information employed in a preceding calculation, as correcting information from said memory means, and calculating the viewpoint anew with said correcting information.

16. A viewpoint detecting method according to claim 15, wherein said stored information comprises information on the pupil diameter.

17. A viewpoint detecting method according to claim 16, further comprising a step for discriminating that said calculation of the viewpoint is not properly conducted, said discrimination step being adapted to identify an error in the viewpoint detection in the case where the pupil diameter is an abnormal value.

18. A viewpoint detecting method according to claim 16, further comprising a step for discriminating that said calculation of the viewpoint is not properly conducted, said discrimination step being adapted to identify an error in the viewpoint detection in the case where the coordinate of the viewpoint are positioned outside an image area.

19. A viewpoint detecting method according to claim 16, further comprising a step for discriminating that said calculation of the viewpoint is not properly conducted, said discrimination step being adapted to identify an error in the viewpoint detection in the case where the distance between the eye and an image area is abnormal.

20. A viewpoint detecting device in which the eye of the user is irradiated with light from a light source, wherein a reflected image of said eye is detected to calculate the viewpoint of the line of sight of the user, comprising:
   memory means for storing information used for calculating the viewpoint in a case where said calculation of the viewpoint is conducted properly; and
   calculation means adapted, in a case that the viewpoint of the user is not able to be calculated, to read the information stored in said memory means and to calculate the viewpoint utilizing said correcting information.

21. A viewpoint detecting device according to claim 20, wherein said memory means is adapted to always store latest information, and wherein said calculation means is adapted to employ said latest information as said correcting information.

22. A viewpoint detecting device according to claim 21, further comprising illumination means for illuminating the eye of the user, and wherein said viewpoint is detected by receiving the light emitted from said illumination means and reflected on the surface of said eye.

23. A viewpoint detecting device according to claim 21, wherein said viewpoint is detected based on a corneal reflected image and the light reflected from the pupil or the iris.

24. A viewpoint detecting device according to claim 21, wherein the information stored in said memory means comprises information on plural pupil diameters.

25. A viewpoint detecting device according to claim 21, wherein said calculation means includes error discrimination means for identifying an error in the viewpoint detection by said viewpoint detecting means, and wherein said error discrimination means is adapted to identify an error in the viewpoint detection in the case where the pupil diameter is an abnormal value, or in the case where the coordinates of the viewpoint are positioned outside the image area of said monitor means, or in the case where the distance between the eye and the image area is abnormal.

26. A viewpoint detecting device according to claim 21, wherein said calculation means includes error discrimination means for identifying an error in the viewpoint detection by said viewpoint detecting means, and wherein said error discrimination means is adapted to correct the output of said viewpoint detecting means with the information stored in said memory means in a case where edges of said pupil cannot be detected in a predetermined number.

27. An image pickup apparatus including a viewpoint detecting device in which the eye of the user is irradiated by light from a light source, and a reflected image of said eye is detected to determine the viewpoint of the line of sight of said user, comprising:

- memory means for storing (i) information used for determining the viewpoint in a case where the calculation of the viewpoint is properly conducted and (ii) luminance information of the taken image in said case;
- light amount detecting means for detecting the luminance of the taken image; and
- calculation means adapted, in a case that the viewpoint of the user is not able to be calculated, to read, from said memory means, the stored information corresponding to the luminance information obtained from said light amount detecting means, and to calculate the viewpoint anew with said correcting information.

28. An apparatus according to claim 27, wherein said viewpoint detection is conducted as a measurement of personal fluctuation information for correcting the personal fluctuation between the eye inclination angle and the visual axis, specific to each user.

29. An apparatus according to claim 27, wherein said calculation means is adapted to detect the relative positional relationship between a corneal reflected image of the eye and the pupil or the iris thereof.

30. An apparatus according to claim 27, wherein the information stored in said memory means comprises information on plural pupil diameters.

31. An apparatus according to claim 27, wherein said calculation means includes error discrimination means for identifying an error in the viewpoint detection by said viewpoint detecting means, and wherein said error discrimination means is adapted to identify an error in the viewpoint detection in a case where the pupil diameter is an abnormal value, or in a case where the coordinate of the viewpoint is positioned outside the image area of said monitor means, or in a case where the distance between the eye and the image area is abnormal.

32. An electronic equipment provided with the viewpoint detecting device according to claim 1.

* * * * *

UNITED STATES PATENT AND TRADEMARK OFFICE
CERTIFICATE OF CORRECTION

PATENT NO. : 5,737,641                    Page 1 of 2
DATED      : April 7, 1998
INVENTOR(S): TAKASHI KOBAYASHI It is certified that error appears in the above-identified patent and that said Letters Patent is hereby corrected as shown below:

At [56] References Cited

FOREIGN PATENT DOCUMENTS

"1241511" should read --1-241511--.
"5285113" should read --5-285113--.
"6034874" should read --6-34874--.
"6138373" should read --6-138373--.
"7031589" should read --7-31589--.

Sheet 8

FIG. 9A, "ELAPESD" should read --ELAPSED--.

Sheet 11

FIG. 11A, "ELAPESD" should read --ELAPSED--.

Column 1

Line 24, "activator" should read --activation--.
Line 38, "further for focussing" should read --function for focusing--.
Line 48, "are" should be deleted.

UNITED STATES PATENT AND TRADEMARK OFFICE
CERTIFICATE OF CORRECTION

PATENT NO. : 5,737,641

DATED : April 7, 1998

INVENTOR(S) : TAKASHI KOBAYASHI

It is certified that error appears in the above-identified patent and that said Letters Patent is hereby corrected as shown below:

<u>Column 4</u>

Line 24, "coincides" should read --coincide--.
    Line 27, "0" should read --0,--.

<u>Column 9</u>

Line 56, "calculation," should read --calculation--.

<u>Column 10</u>

Line 10, "calcula-" should read --the calcula- --.
    Line 11, "improper" should read --as improper--.

Signed and Sealed this

Twenty-ninth Day of December, 1998

Attest:

BRUCE LEHMAN

*Attesting Officer*      *Commissioner of Patents and Trademarks*